United States Patent [19]

Metelnick

[11] 4,224,935
[45] Sep. 30, 1980

[54] BAG PROTECTOR FOR LEG CAST

[76] Inventor: John A. Metelnick, 724 Clinton Pl., Evanston, Ill. 60201

[21] Appl. No.: 44,568

[22] Filed: Jun. 1, 1979

[51] Int. Cl.³ .............................................. A61F 13/00
[52] U.S. Cl. ..................................... 128/82; 128/165; 36/7.1 R
[58] Field of Search .................... 128/82, 157, 165, 83, 128/83.5, DIG. 20; 36/8.1, 7.3, 4, 110, 7.1 R, 7.7, 70 R, 59 R; 2/61, 239, DIG. 7

[56] References Cited

U.S. PATENT DOCUMENTS

| | | | |
|---|---|---|---|
| 1,068,942 | 7/1913 | Siegel | 36/7.1 R |
| 2,075,229 | 3/1937 | Rose | 36/8.1 |
| 2,176,463 | 10/1939 | Meendsen | 36/7.1 R |
| 2,229,575 | 1/1941 | Kaplan | 128/82 |
| 2,746,173 | 5/1956 | Tranmal | 36/8.1 |
| 2,986,823 | 6/1961 | Kos | 36/7.1 R |
| 3,324,580 | 6/1967 | Baxter | 36/8.1 |
| 3,497,875 | 3/1970 | Rivera | 2/239 |
| 3,735,759 | 5/1973 | MacKay | 128/82 |
| 3,741,203 | 6/1973 | Liman | 128/82 |
| 3,747,125 | 7/1973 | Goldman et al. | 2/61 |
| 3,906,941 | 9/1975 | Cook, Jr. | 128/82 |
| 4,036,220 | 7/1977 | Bellasalma | 128/82 |

FOREIGN PATENT DOCUMENTS 330213  6/1930  United Kingdom .................... 36/70

*Primary Examiner*—Robert W. Michell
*Assistant Examiner*—Arthur S. Rose
*Attorney, Agent, or Firm*—McWilliams, Mann & Zummer

[57] ABSTRACT

A bag protector for leg casts, for use in bathing or other manners of water immersion, comprising a tube of polyethylene of film thickness dimensions having oppositely disposed side edge pleats and oppositely disposed wide side walls separated by the edge pleats, both of which extend longitudinally of the bag in flattened relation in the dormant condition of the bag, with one end of the tube being freely openable and trimmable, and the other end of the tube being formed to define a sealed, closed end seam transversely thereacross that includes said pleats. The tube thus defines a pair of juxtaposed side panels extending longitudinally of same that are separated along the edges of the bag by the folding side edge pleats. The bag at its closed end has applied to same, sole fashion, on either side of the sealing seam, resilient padding in sheet form having antiskid characteristics for aiding the user against slippage when moving over wet surfaces.

7 Claims, 5 Drawing Figures

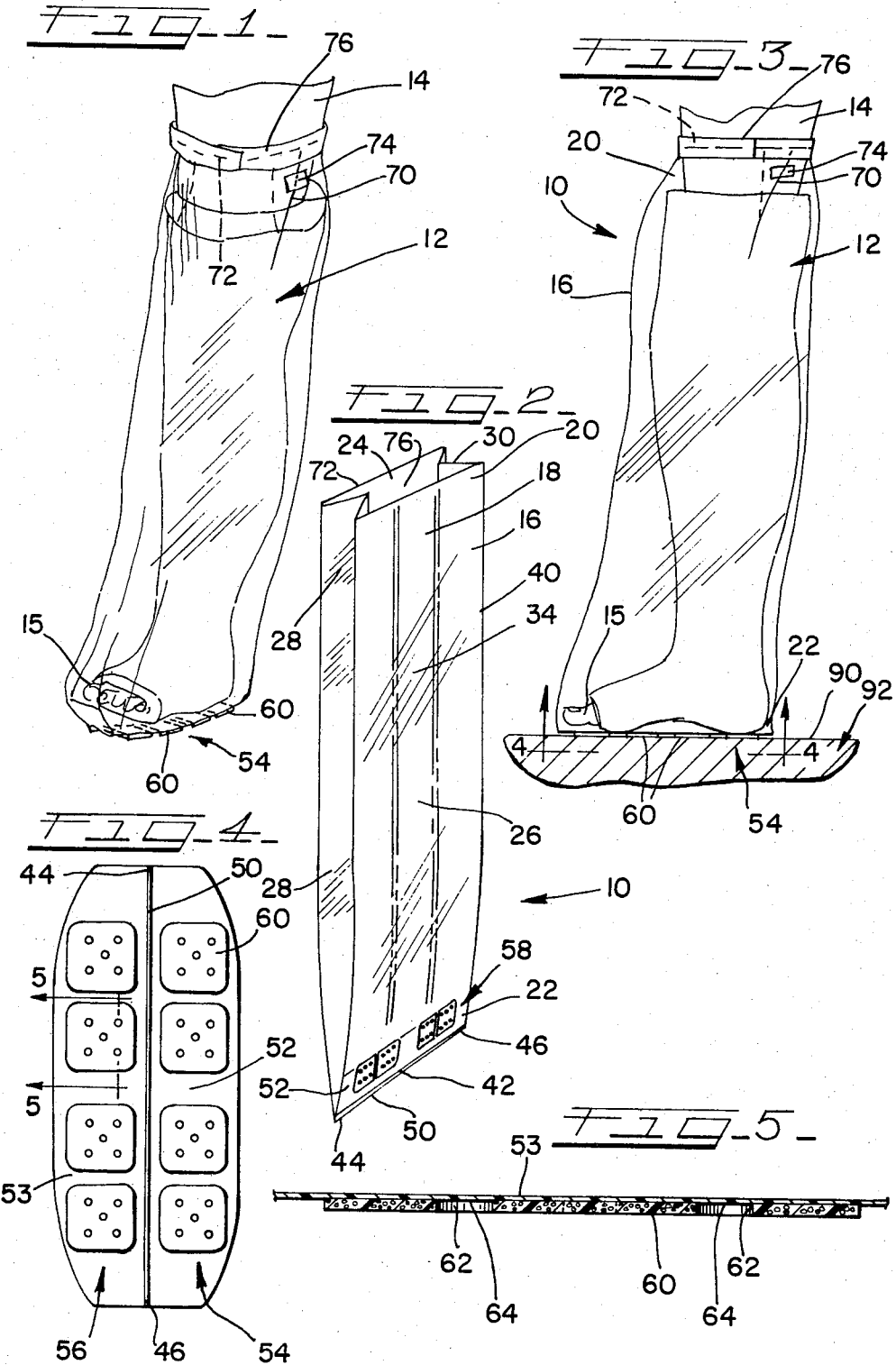

BAG PROTECTOR FOR LEG CAST

This invention relates to a bag protector for leg casts, and more particularly, to a bag arrangement for application to leg casts to protect the cast when the wearer wishes to bathe.

One of the major difficulties faced by persons wearing a leg or arm cast is the problem of bathing. Leg and arm casts are customarily formed by water soluable plaster material which is thus highly susceptible to damage and possible disintegration when it becomes wet.

Numerous efforts have been made to devise cast protectors in the form of covers for enabling the user to bathe without adversely affecting his cast, as illustrated by U.S. Pat. Nos. 3,324,580, 3,329,144, 3,747,125, 3,785,374, 3,906,941, 4,036,220, and 4,043,326.

However, the problem has continued as existing protecting cast covers are expensive, are frequently not available, when needed, and tend to be complicated and inclined to be easily damaged, thereby limiting useability from a practical standpoint.

One serious problem that existing cast covers have not adequately dealt with is the potential for slipping when the person having the cast is getting around in the bathing area. The moisturized or water covered floor surfaces occasioned in bathing are conducive to slipping, especially for those impeded by leg casts, with the resulting high potential of serious injury should a fall occur.

A principal object of this invention is to provide a leg cast protector of the bag type that is not only simply and easily applied by the cast wearer himself, but which also gives the cast wearer assurance of protection against slipping or skidding of the cast bearing limb when getting about a bathing or other area where excessive moisture will make walking slippery.

Another important object of the invention is to provide a low-cost simplified cast protector of the bag type that may be conveniently made widely available on a mass basis and readily applied for full waterproofing protection of the cast.

Another important object of the invention is to provide a bag-type leg cast protector that is applied by being pulled over the cast and sealed to the user's leg above the cast by smoothing the bag entry end against the user's skin and keeping same in place above the margin of the cast for sealing purposes using standard hospital adhesive tape.

Yet other objects of the invention are to provide a leg cast protector that is readily adjustable to accommodate normal and large limbs, that may be used for both leg and arm casts while providing for protection against accidental slippage when used for leg casts, and that is economical to manufacture, simple to use, and reuseable in nature.

In accordance with the invention, a cast protector is provided comprising a bag in the form of an elongate flat tube formed from polyethylene of film thickness dimensions that is shaped to have a pair of oppositely disposed V-pleats forming the side edges of the bag which extend the length of same. The bag thus is formed to define a pair of opposed side walls which also extend the length of same and are juxtaposed, with the bag's side edge pleats each folded closed in the dormant condition of the bag. The tube is readily openable at one end of same and at the other end of same, the tube is sealed closed to define a sealed end seam that extends the width of the bag sidewalls and closes off the bag side edge pleats as well.

The bag at its closed end has applied on the exterior of its said sidewalls and adjacent to and on either side of the said end seam a pair of layers of resilient padding in sheath form having antiskid characteristics. The padding is formed with a plurality of spaced apart perforations that each expose the bag sidewalls underlying same to define spaced suction pockets that come into play when the bag is used.

When the cast protector is used for a leg cast, the bag before being applied to the limb bearing the cast is laid on same for measuring purposes, and the openable end of same trimmed off as needed to allow coverage of the limb up to above the cast for 4–8 inches or so above or beyond the cast. This determines where the tape that seals the bag open end will contact the user's skin; body hair at this location may then be removed by shaving to insure a tight water sealing action when the bag sealing tape is applied, and to accommodate ready removal of the tape after bathing. The bag is then applied to the limb bearing the cast, by opening the trimmed openable end of the bag, orienting the bag such that its width dimension is aligned with the user's foot lengthwise of the foot, inserting the foot in the bag, and pulling the bag over the cast to the position where the user's foot seats against the bag end seam. The bag side edge pleats open up or unfold as the user's leg is moved the length of the bag, with the bag sidewall portions bearing the antiskid padding swinging outwardly of the bag about the bag sealed end seam as an axis to dispose the padding sole fashion on either side of the seam in substantial coplanar relation for floor engagement that will take place after the application of the bag to the limb is completed. The bag open end is pulled over and above the cast to its full trimmed length, with a tuck or fold then being made in the bag open end to draw the bag open end in close fitting relation about the user's leg and firmly against the user's skin, with this tuck being initially held in place by a small piece of tape. The application of the bag is completed by winding hospital tape or the like about the bag open end, with one-half of the width of the tape being applied against the bag end, and the other half of the tape being adhered to the user's skin. The finger pressing of the tape fully about the bag end in question as well as against the user's skin in this area should be employed to insure uniform adhesion of the tape thereabout for full sealing purposes.

Where the user bathes using a shower, as the water flow involved is downward over the taped bag connection to the user's leg skin, normal care in applying the tape to seal the bag open end to the user's leg should fully protect the cast from exposure to the shower water.

Where bathtub bathing is desired, initial testing of the seal at the taped end of the bag will be desirable, with further tape application being employed as necessary to insure an adequate seal, keeping in mind that the seal joint between bag open end and the user's leg skin will be subject to water pressure when the user is in the bathtub.

In any event, when the user moves about the bathing area, to the extent he is able to place his weight on the limb bearing the cast, the antiskid or antislip characteristics of the bag sole padding resist slipping tendencies. The padding compresses under the user's weight to bring the portions of the bag sidewalls exposed by the padding perforations into a suction relation with the floor surface involved, which gives the cast protecting cover a purchase on the floor surface that, even though such surface is wet, will resist slipping tendencies.

Still other objects, uses and advantages will be obvious or become apparent from the consideration of the following detailed description and the application drawing.

In the drawing:

FIG. 1 is a perspective view showing one embodiment of the invention as applied to an individual's leg cast in practicing the invention;

FIG. 2 is a perspective view of the cast protector itself in a laid out, partially open, condition;

FIG. 3 is a side elevational view of the cast protector as shown in FIG. 1;

FIG. 4 is a bottom plan view of the cast protector shown in FIG. 3, as taken along line 4—4 of FIG. 3; and FIG. 5 is a fragmental section view taken substantially along the line 5—5 of FIG. 4.

However, it is to be distinctly understood that the specific drawing illustrations provided are supplied primarily to comply with the requirements of the Patent Laws, and that the invention has other embodiments that will be obvious to those skilled in the art, and which are intended to be covered by the appended claims.

Reference numeral 10 of FIG. 2 indicates the cast protector of this invention in its dormant form, with FIGS. 1 and 3 illustrating the protector as applied to a leg cast 12 of an individual's leg 14, for purposes of protecting the cast 12 when the individual wishes to bathe.

The protector 10 is in the form of a bag 16 defined in the illustrated embodiment by a flattened tube 18 formed from a suitable water-resistant plastic polymer material. The tube 18 is preferably formed from polyethylene sheeting of film thickness dimensions, with a film thickness on the order of 0.003–0.004 inch being preferred.

In the showing of the bag 16 that is made in the drawings, the bag is shown to be transparent for ease of illustration, but it is understood that the polyethylene material employed may be opaque and tinted or colored to suit as desired.

The tube 18 has its end 20 openable for insertion of the user's leg and cast carried by same into the bag 16, and a closed end 22 against which the foot 15 of the user's leg, whether or not included in the cast, is to seat when the cover 10 is applied to the leg.

The tube 18 is shaped to define a pair of opposed wide sides 24 and 26 which extend longitudinally of the bag between its ends 20 and 22, which are separated by a pair of opposed V-shaped pleats 28 and 30, which also extend between the ends 20 and 22 of the bag. In the partially opened condition of the bag, the pleats 28 and 30 are in the partially unfolded relation shown in FIG. 2; however, in the dormant condition of the bag, the pleats 28 and 30 are fully folded closed so that the tube 18 is in flattened relation for convenience of handling and packaging. In this condition, the cover 10 may be rolled or folded up for packaging purposes that may be desired.

The tube 18 is subdivided into a pair of opposed sidewalls 34 and 36 of uniform width extending between and to the respective bag ends 20 and 22, which are separated along the side edges 38 and 40 by the respective side edge pleats 28 and 30 that in effect form the side edges 38 and 40 of the tube along the length of the tube.

The tube 18 at its end 20 is free from sealing or other closure structures so as to be readily openable when the protector 10 is to be applied to a leg cast.

The tube 18 at its end 22 is formed with closed end seam 42 that extends across the entire width of the tube including the pleats 28 and 30. The seam 42 is formed by utilizing suitable heat sealing techniques to firmly bond together the sidewalls 34 and 36 transversely across the tube including across the pleats 28 and 30 which are both sealed closed at the closed corners 44 and 46 of the cover 10. The seam 42 is made fluid resistant in nature and thus provides a water-in flow resisting seal across the tube end 22 to completely seal the cover 10 at its closed end. The abutting layers of the polyethylene that are bonded together at seam 42 define an end flange 50 of limited length that projects longitudinally of the cover 10.

Further in accordance with the invention, the sidewalls 34 and 36 at the portions 52 and 53 thereof that are adjacent at either side of the seam 42 have bonded to same the resilient padding layers in sheath form that are generally indicated by reference numerals 54 and 56 in FIG. 4, and by reference numeral 58 in FIG. 2 (only one side of the bag being shown in FIG. 2, it being understood that the other side of the bag is similarly arranged).

The resilient padding layers illustrated are in the form of sheathing segments 60 and in the preferred embodiment are made up of granulated cork uniformly dispersed in a suitable synthetic neoprene rubber compound, the materials of which are selected so that the padding is resistant to aromatic products and oil products. This material is sold commercially, and one supplier is Deccofelt Corporation of Glendora, Calif.

The individual pads 60 are formed with a plurality of spaced apart perforations 62 which extend entirely through the individual pads 60 to expose limited areas 64 of the bag sidewall portions 52 and 53, respectively, as indicated in FIG. 5.

The individual pads 60 in the form of FIG. 4 are applied in the indicated spaced apart relation there shown, with the padding layer 58 of FIG. 2 illustrating another manner of applying the pads 60 in their operative position. Of course, the padding layers 54 and 56 could be formed by continuous strips of the padding material involved if so desired.

In any event, the function of the padding layers 54, 56 and 58 is to provide antiskid or antislip characteristics for the cover 10, as will now be described.

In one preferred form of the invention, the bags 16 are made 42 inches in length with a 32 inch circumference about the bag, thus dimensioning the cover 10 for an application to adult legs of normal and large sizes; in a smaller form, in accordance with the invention, the bag is 30 inches in length with a 22 inch circumference for application to legs of children and small sized adults. The covers 10 are also adapted for use in connection with arm casts, with the medium sized bag employed being made appropriate for the arm dimensions encountered.

In employing the cover 10 to protect a leg cast, when the user wishes to bathe, a cover 10 is selected and laid in its unopened condition along the leg cast for measuring purposes. It is preferred that the cover that is applied to the leg bearing the cast extend 4 to 8 inches above the cast. The appropriate measurement is made with regard to the bag open end 20 and then the bag open end trimmed accordingly.

The bag 16 is then opened at its end 20 and oriented to dispose the side edges 38 and 40 of the bag in alignment with the lengthwise dimension of the user's foot 15, which thus positions the seam 42 in the same alignment with the user's foot 15. The bag is then pulled over the user's foot 15, and cast 12, up to the relative positioning indicated in FIGS. 1 and 2, with the bag being pulled along its length to firmly seat the user's foot 15 against the closed end 22 of the bag, and specifically against the seam 42. This action has the effect of swinging the bag sidewall portions 52 and 53 outwardly of the bag about the seam 42 as an axis to dispose the padding layers 54, 56 and 58 sole fashion for engagement with the floor surface that the user's leg 14 is to rest or step on.

At the top end of the now applied bag, represented by the open end 20 of the bag, a tuck or pleat is made in the bag sidewall where indicated at 70 so that the open end of the bag can be smoothly and firmly wrapped about and against the skin of the user's leg 14 at its marginal edge 72, after which a short piece of tape 74 is applied over the tuck 70 to hold it in place.

The marginal edge 72 of the bag is then sealed with respect to the skin of the user, by applying a suitable pressure sensitive tape 76 about the marginal edge 72 of the bag, with one half of the tape width adhering to the bag, and the other half of the tape width adhering to the user's skin. In this connection, 2 inch wide hospital tape is recommended for this application, with the tape being applied entirely about the circumference of the user's leg to achieve a full water seal about the bag end 20.

The cast 12 is now protected for shower bathing, as shower water moving downwardly over the tape 76 is adequately shed and prevented from entering the bag 20 by the nature of the seal formed by tape 76.

Where bathtub bathing is preferred, additional taping may be necessary at the marginal edge 72 of the bag. This is because when the user is in the bathtub with the leg bearing the cast in the water, there will be water pressure bearing against the tape joint represented by the tape 76. It is adviseable to initially test the effectiveness of the seal that is made, by the user by applying the tape 76, to check for leakage before actual bathing begins. This may be done by lowering the leg 14 into the water and watching for air bubbles. If necessary, the leg 14 is removed, dried in the area of the cover open end 20, and additional tape added for improved sealing purposes.

The antiskid characteristics of the cover 10 are of special significance.

Assuming that the cover 10 is applied as indicated in FIGS. 1 and 3, the user places the leg involved on the surface 90 of floor 92, as the user bears against the floor surface 90, the sheathing segments 60 are compressed against the floor thus becoming reduced in thickness dimension. When the user takes the weight off his leg that bears cover 10, during this process the segments 60 tend to return to their original thickness. However, as a result of the compression of the segments 60, the space defined by the perforations 62 will have been reduced, with the result that as the segments 60 return to their normal thickness on the release of foot pressure against the floor surface 90, vacuum conditions are created within the spaces defined by the perforations 60 due to the seal over the perforations that has been provided by the areas 64 of the bag side wall portions 52 and 53 that are exposed by the perforations 62.

The result is that the cover 10 is applied to the user's leg will tend to adhere to the floor surface 90 with a suction cup-like action in the area of each perforation 62 that is applied against the surface 90, which suction action overcomes slippage tendencies, even on very moist floor surfaces such as would be encountered adjacent a shower or bathtub bathing area. As a matter of fact, the presence of moisture on the floor surface enhances the suction action provided by the sheathing segments 60.

It will therefore be seen that the invention provides a simple yet effective leg cast cover that is easy and safe to use and that provides effective antislipping protection that is so badly needed by those having to wear a leg cast when they must move around in a bathing area where the floor is likely to be slippery due to excess moisture presence. Examples are shower and bath areas; however, the device finds obvious utility at swimming pools, beaches, and when using boating facilities, for example. The device is also useable as an emergency covering for limb casts.

The device provided by the invention is inexpensive to manufacture and may be readily available at low cost to all facilities where persons with injured limbs need covers of this type to protect their casts while bathing or engaging in activities where significant moisture presence will be involved.

The covers 10 are reuseable in nature, the user merely having to remove the attaching tape with sufficient care so that no undue tearing of the bag is effected. If limited tearing does happen, some trimming of the bag top ordinarily is permissible for reuse, depending on how much the user left at the top of the bag in making his first use.

While the covers 10 as illustrated are designed for leg use, it will be apparent that they are also adapted for use on arm casts.

The foregoing description and the drawings are given merely to explain and illustrate the invention and the invention is not to be limited thereto, except insofar as the appended claims are so limited, since those skilled in the art who have the disclosure before them will be able to make modifications and variations therein without departing from the scope of the invention.

I claim:

1. A cover for enclosing a cast on a limb of the user, said cover comprising:

an elongate flat tube of water impermeable flexible material having a pair of oppositely disposed side edge pleats extending longitudinally of same for the length of same, said tube at one end of same being freely openable and at the other end of same having opposite sides of said tube rectilinearly bonded together across the width of said tube including said pleats to define a sealed closed end seam at said other end of said tube, said tube thereby defining a pair of opposed side walls of uniform width extending between said ends of said tube and respectively separated along the length of the tube by the respective side edge pleats that thereby define longitudinally extending side edges of the tube that extend the length of said tube, said tube side walls adjacent said closed end seam each having secured to the exterior or same a length of resilient padding in sheet form having a plurality of perforations exposing the respective side walls, whereby the limb may be inserted into the tube through said open end thereof to bring the distal end of the limb against said closed end seam with said tube side edges unfolding as the tube is drawn over the limb to open up the tube to the limb for enclosing the cast, in said tube side walls of said tube other end swing away from each other about said seam as an axis as the limb distal end engages said seam interiorily of the tube to dispose said padding layers for supporting the limb through the tube.

2. The cover set forth in claim 1 wherein:
said tube is of one piece construction formed from polyethylene of film dimensions.

3. The cover set forth in claim 1 wherein:
said padding layers each comprise sheeting composed of granulated cork disposd in a neoprene binder compound.

4. The cover set forth in claim 2 wherein:
said polyethylene has a thickness on the order of 0.003–0.004 inch.

5. The cover for enclosing a leg cast of the user, said cover comprising:
an elongate flat tube formed from water impermeable flexible material of film thickness dimensions and formed to have a pair of oppositely disposed V pleats extending longitudinally of same for the length of same,
said tube at one end of same being openable for access into the interior of said tube and said tube at the other end of same having opposite sides of said tube rectilinearly bonded together across the width of said tube including said pleats to form a sealed closed end seam at and across said other end of said tube and disposed to position said tube sides in juxtaposition,
said tube thereby defining a pair of opposed side walls of uniform width extending between said ends of said tube and respectively separated along the length of said tube about its circumference by the respective side edge pleats that thereby define longitudinally extending side edges of the tube that extend the length of the tube,
said tube side walls adjacent said closed end seam each having secured to the exterior of same a layer of resilient padding having antiskid characteristics in sheet form, said layers thereby being disposed on either side of the closed end seam, said layers being formed to define a plurality of perforations exposing the tube respective side walls,
whereby the user may insert his leg bearing the cast into the cover by opening the cover one end and aligning the foot of said leg with the cover pleats and then pulling the cover up over the leg cast to seat the foot of the leg against said end seam whereupon said tube side walls of said tube other end are swung away from each other about said seam as an axis to substantially coplanar relation to dispose said padding layers for floor engagement under the weight of the user when in an upright position, with said one end of said cover being taped in close fitting relation about and to the user's said leg above the cast for closing the cover about the cast, said padding layers under the weight of the user compressing to dispose the portions of said tube side walls exposed thereby in suction relation with the floor.

6. The cover set forth in claim 5 wherein:
said padding layers each comprise sheeting composed of granulated cork dispersed in a neoprene binder compound.

7. The cover set forth in claim 5 wherein:
the tube is of one piece construction formed from polyethylene of film dimensions.

* * * * *